US012453645B2

(12) United States Patent
Amaral et al.

(10) Patent No.: US 12,453,645 B2
(45) **Date of Patent: *Oct. 28, 2025**

(54) TRIAL NECK AND METHOD

(71) Applicant: DePuy Ireland Unlimited Company, Ringaskiddy (IE)

(72) Inventors: Francisco Amaral, Acushnet, MA (US); Alec Birkbeck, Leeds (GB); Philippa Clarkson, Leeds (GB); Graeme Dutton, Burnley (GB); Natasha Fell, Penrith (GB); Caroline Wither, Leeds (GB); Neil Woollen, Bradford (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 946 days.

This patent is subject to a terminal disclaimer.

(21) Appl. No.: 17/649,254

(22) Filed: Jan. 28, 2022

(65) Prior Publication Data

US 2022/0249256 A1 Aug. 11, 2022

Related U.S. Application Data

(63) Continuation-in-part of application No. 17/248,665, filed on Feb. 2, 2021, now Pat. No. 11,931,268.

(51) Int. Cl.
*A61F 2/46* (2006.01)
*A61F 2/36* (2006.01)

(52) U.S. Cl.
CPC .......... *A61F 2/4684* (2013.01); *A61F 2/4607* (2013.01); *A61F 2002/3647* (2013.01); *A61F 2002/3652* (2013.01); *A61F 2002/3674* (2013.01)

(58) Field of Classification Search
CPC ............ A61F 2/4684; A61F 2002/3652; A61F 2002/30607; A61F 2002/30614; A61F 2002/30616
See application file for complete search history.

(56) References Cited

U.S. PATENT DOCUMENTS 5,100,407 A 3/1992 Conrad
5,336,268 A 8/1994 Rispeter
5,569,263 A * 10/1996 Hein .................. A61B 17/1659 606/85

(Continued)

FOREIGN PATENT DOCUMENTS

DE 202007009646 U1 10/2007
DE 102007032014 B3 * 10/2008 ......... A61B 17/1659

(Continued)

*Primary Examiner* — Alvin J Stewart
(74) *Attorney, Agent, or Firm* — Barnes & Thornburg LLP

(57) ABSTRACT

A trial neck for hip surgery and a method of attaching a trial neck to a femoral canal implement. The trial neck includes a body portion including a bore for receiving a proximal end of a femoral canal implement. The trial neck also includes an elongate neck extending from the body portion. The trial neck further includes a locking mechanism comprising a lever. The lever has a first end. The lever also has a second end. The lever further has an engagement surface. The second end of the lever is actuable to urge the engagement surface against the proximal end of the femoral canal implement to secure the proximal end of the femoral canal implement within the bore.

17 Claims, 11 Drawing Sheets

(56) References Cited

U.S. PATENT DOCUMENTS

| | | | | |
|---|---|---|---|---|
| 5,645,607 | A | 7/1997 | Hickey | |
| 5,658,352 | A | 8/1997 | Draenert | |
| 5,746,771 | A | 5/1998 | Clement, Jr | |
| 5,766,261 | A | 6/1998 | Neal | |
| 5,800,556 | A * | 9/1998 | Sanders | A61F 2/4684 606/89 |
| 5,888,211 | A * | 3/1999 | Sanders | A61F 2/4684 623/22.4 |
| 6,090,146 | A | 7/2000 | Rozow, III et al. | |
| 6,117,138 | A | 9/2000 | Burrows | |
| 6,193,759 | B1 | 2/2001 | Ro | |
| 6,977,000 | B2 | 12/2005 | Vanasse | |
| 7,425,214 | B1 * | 9/2008 | McCarthy | A61F 2/4684 606/89 |
| 7,981,161 | B2 | 7/2011 | Choi | |
| 8,449,619 | B2 * | 5/2013 | Metcalfe | A61B 17/162 623/22.11 |
| 9,439,785 | B2 | 9/2016 | Huddle | |
| 11,344,437 | B2 * | 5/2022 | Bailey | A61B 17/1659 |
| 11,602,359 | B2 * | 3/2023 | Clements | A61B 17/1659 |
| 11,931,268 | B2 * | 3/2024 | Board | A61F 2/3609 |
| 2003/0088316 | A1 | 5/2003 | Ganjianpour | |
| 2004/0054419 | A1 | 3/2004 | Serra | |
| 2004/0064186 | A1 * | 4/2004 | McCleary | A61B 17/1659 623/18.11 |
| 2004/0122440 | A1 * | 6/2004 | Daniels | A61F 2/4684 606/102 |
| 2004/0267267 | A1 * | 12/2004 | Daniels | A61B 17/1617 623/22.42 |
| 2006/0004459 | A1 * | 1/2006 | Hazebrouck | A61F 2/36 623/23.45 |
| 2006/0241625 | A1 * | 10/2006 | Metcalfe | A61F 2/4684 606/79 |
| 2006/0267267 | A1 | 11/2006 | Koga | |
| 2008/0133023 | A1 | 6/2008 | Schlotterback | |
| 2012/0259338 | A1 | 10/2012 | Carr | |
| 2012/0259424 | A1 * | 10/2012 | Hood | A61F 2/4684 623/23.35 |
| 2012/0290099 | A1 | 11/2012 | Gibson | |
| 2015/0018961 | A1 * | 1/2015 | Huddle | A61F 2/4684 623/22.4 |
| 2016/0262912 | A1 * | 9/2016 | Burnikel | A61F 2/4684 |
| 2019/0117412 | A1 | 4/2019 | Zimmerman | |
| 2019/0231540 | A1 | 8/2019 | Kim | |
| 2020/0276029 | A1 * | 9/2020 | Bailey | A61F 2/3609 |
| 2020/0345517 | A1 * | 11/2020 | Morrisey | A61F 2/4684 |
| 2020/0352742 | A1 * | 11/2020 | Horne | A61F 2/4607 |
| 2022/0233337 | A1 * | 7/2022 | Dmuschewsky | A61F 2/3601 |
| 2022/0241092 | A1 * | 8/2022 | Board | A61F 2/3609 |
| 2022/0249256 | A1 * | 8/2022 | Amaral | A61F 2/4607 |
| 2022/0346976 | A1 * | 11/2022 | Naylor | A61F 2/3662 |
| 2022/0346977 | A1 * | 11/2022 | Morrisey | A61F 2/4684 |

FOREIGN PATENT DOCUMENTS

| | | | | |
|---|---|---|---|---|
| EP | 1013242 | A2 | 6/2000 | |
| FR | 2788429 | A1 | 7/2000 | |
| FR | 2796267 | A1 * | 1/2001 | A61B 17/1659 |
| FR | 2963733 | A1 * | 2/2012 | A61B 17/1659 |
| FR | 3043545 | A1 | 5/2017 | |
| FR | 2660857 | A1 * | 3/2025 | A61F 2/46 |
| JP | 2003010215 | A | 1/2003 | |
| JP | 2012165889 | A | 9/2012 | |
| JP | 2013094331 | A * | 5/2013 | A61F 2/4684 |
| JP | 5859810 | B2 | 2/2016 | |
| WO | WO-2019034769 | A1 * | 2/2019 | A61F 2/46 |
| WO | WO-2019057698 | A1 * | 3/2019 | A61F 2/46 |
| WO | WO-2020193004 | A1 * | 10/2020 | A61F 2/36 |
| WO | WO-2020193005 | A1 * | 10/2020 | A61F 2/46 |

* cited by examiner

TRIAL NECK AND METHOD

CROSS REFERENCE TO RELATED PCT APPLICATION

This application is a continuation-in-part to U.S. patent application Ser. No. 17/248,665, filed Feb. 2, 2021, which is incorporated by reference in its entirety.

BACKGROUND

The present specification relates to a trial neck and to a method of attaching a trial neck to a femoral canal implement.

Hip replacement is a surgical procedure in which the hip joint is replaced by a prosthetic implant. Total replacement of the hip joint involves installing an acetabular cup implant in the acetabulum of a patient and installing a prosthetic in the femur of the patient. The prosthetic typically includes a stem, which is received in the medullary canal of the femur, and a head having a bearing surface which is received in the acetabulum or acetabular cup implant. The prosthetic typically also includes a neck which extends between a proximal end of the stem and the head.

Successful hip replacement surgery requires correct positioning and alignment of the acetabular cup implant as well as the prosthetic itself. Misalignment and/or the selection of an inappropriately sized acetabular cup implant and/or the prosthetic may result is restricted movement of the prosthetic and/or accelerated wear and tear of the bearing surfaces of the acetabular cup implant and the bearing surface of the head. Various factors are involved in achieving this correct positioning and alignment. At least some of these factors relate to the neck of the prosthetic. These factors may include, for instance, the length of the neck (offset), and an angular orientation of the neck relative to the stem.

Hip replacement surgery usually involves trialing the various components of the acetabular cup implant and the prosthetic. As part of this, various sizes of broach/reamer may be used to prepare the medullary canal of the femur. Once the broach/reamer is inserted in the femur, a trial neck and trial head may also be attached to the broach/reamer, in order to evaluate whether a prosthetic having a neck and head of that type (e.g. in terms of the size and offset of the neck) would appropriate for the patient.

After the surgeon is satisfied that the chosen combination of broach/reamer, trial neck and trial head are correctly positioned and aligned, they may be removed and replaced with the implant itself.

SUMMARY

Aspects of the present disclosure are set out in the accompanying independent and dependent claims. Combinations of features from the dependent claims may be combined with features of the independent claims as appropriate and not merely as explicitly set out in the claims.

According to an aspect of the present disclosure, there is provided a trial neck for hip surgery, the trial neck comprising:

- a body portion including a bore for receiving a proximal end of a femoral canal implement;
- an elongate neck extending from the body portion;
- a locking mechanism comprising a lever having:
  - a first end;
  - a second end; and
  - an engagement surface,
- wherein the second end of the lever is actuable to urge the engagement surface against the proximal end of the femoral canal implement to secure the proximal end of the femoral canal implement within the bore.

A lever of the locking mechanism of the trial neck may provide a secure way of attaching the trial neck to a femoral canal implement. The lever can allow a sufficient securing force to be applied to the femoral canal implement within the bore, while also allowing fine adjustments to be made.

The locking mechanism may further include an actuation member for engaging with the second end of the lever to actuate the lever. This can provide a convenient way of operating the lever.

The trial neck may include a further bore. The actuation member may extend within the further bore. The further bore may extend within the elongate neck.

The further bore may extend substantially parallel to a longitudinal axis of the elongate neck.

A proximal end of the elongate neck may have an opening leading to the further bore. A proximal end of the actuation member may include a connection feature for connecting a tool to the actuation member for actuating the actuation member.

The proximal end of the elongate neck may be configured to be attached to a trial head.

The further bore may have a threaded surface. The actuation member may have a threaded surface for engaging with the threaded surface of the further bore to allow the actuation member to be rotated to move the actuation member along the further bore to engage with the second end of the lever. The threaded engagement of the actuation member can allow fine adjustments to be made to the position of the lever.

The trial neck may have a window for viewing the actuation member within the further bore. This can be useful also for cleaning of the trial neck between surgical procedures.

The first end of the lever may be located at a lateral side of the trial neck.

The engagement surface of the lever may be curved to conform with a curved outer surface of the proximal end of the femoral canal implement.

An inner surface of the bore may have a profiled surface for engaging with a corresponding profiled outer surface of the proximal end of the femoral canal implement to prevent rotation of the femoral canal implement with respect to the trial neck about a longitudinal axis of the femoral canal implement.

The first end of the lever may be integral with the body portion. The engagement surface may be located intermediate the first end of the lever and the second end of the lever.

The second end of the lever may be located within the elongate neck.

The lever may include at least one dog leg bend. This can allow the lever arm provided by the lever to be optimised.

The femoral canal implement may, for example, be an implant such as a stem implant. The femoral canal implement may, for example, be femoral canal preparation instrument such as a reamer, a trial stem, or a broach.

The first end of the lever may be pivotably mounted within the trial neck.

The actuation member may have a distal end for engaging with the second end of the lever to actuate the lever. The distal end may include an indentation for engaging with a corresponding protrusion on the second end of the lever to move the engagement surface away from the proximal end of the femoral canal implement on withdrawal of the actuation member along the further bore.

The second end of the lever may include an actuation member receiving opening.

The first end of the lever may include a grippable feature for manually actuating the lever to move the engagement surface away from the proximal end of the femoral canal implement.

The second end of the lever may include an angled surface facing toward the bore, to allow the proximal end of the femoral canal implement to ride upon the angled surface to pivot the lever to move the engagement surface away from the proximal end of the femoral canal implement upon insertion of the proximal end of the femoral canal implement into the bore.

The lever may further comprise a biasing element for biasing the first end of the lever toward the bore, thereby to bias the engagement surface away from the bore.

According to another aspect of the present disclosure, there is provided a surgical kit comprising:

- a trial neck of the kind set out above; and
- a femoral canal implement.

The proximal end of the femoral canal implement may include a circumferential lip or groove for engagement with the engagement surface of the locking mechanism of the trial neck. The engagement surface may catch against the lip or groove when the locking mechanism is locked, to resist removal of the proximal end of the femoral canal implement from the bore.

The femoral canal implement may, for example, be an implant such as a stem implant. The femoral canal implement may, for example, be femoral canal preparation instrument such as a reamer, a trial stem, or a broach.

According to a further aspect of the present disclosure, there is provided a method of attaching a trial neck to a femoral canal implement, the trial neck comprising:

- a body portion including a bore for receiving a proximal end of a femoral canal implement;
  - an elongate neck extending from the body portion;
  - a locking mechanism comprising a lever having:
    - a first end;
    - a second end; and
    - an engagement surface,
  - wherein the second end of the lever is actuable to urge the engagement surface against the proximal end of the femoral canal implement to secure the proximal end of
- the femoral canal implement within the bore, the method comprising:
- inserting the proximal end of the femoral canal implement into the bore; and
- actuating the second end of the lever to urge the engagement surface against the proximal end of the femoral canal implement.

A lever of the locking mechanism of the trial neck may provide a secure way of attaching the trial neck to a femoral canal implement. The lever can allow a sufficient securing force to be applied to the femoral canal implement within the bore, while also allowing fine adjustments to be made.

The method may include engaging an actuation member of the locking mechanism with the second end of the lever to actuate the lever. This can provide a convenient way of operating the lever.

A proximal end of the actuation member may include a connection feature. The method may further include connecting a tool to the actuation member to the connection feature for actuating the actuation member.

The method may further include viewing the actuation member through a window in the elongate neck of the trial neck.

The engagement surface of the lever may be curved to conform with a curved outer surface of the proximal end of the femoral canal implement.

The first end of the lever may be integral with the body portion. The engagement surface may be located intermediate the first end of the lever and the second end of the lever.

The first end of the lever may be pivotably mounted within the trial neck.

The femoral canal implement may, for example, be an implant such as a stem implant. The femoral canal implement may, for example, be femoral canal preparation instrument such as a reamer, a trial stem, or a broach.

BRIEF DESCRIPTION OF THE DRAWINGS

Embodiments of this disclosure will be described hereinafter, by way of example only, with reference to the accompanying drawings in which like reference signs relate to like elements and in which.

DETAILED DESCRIPTION

Figure 1:
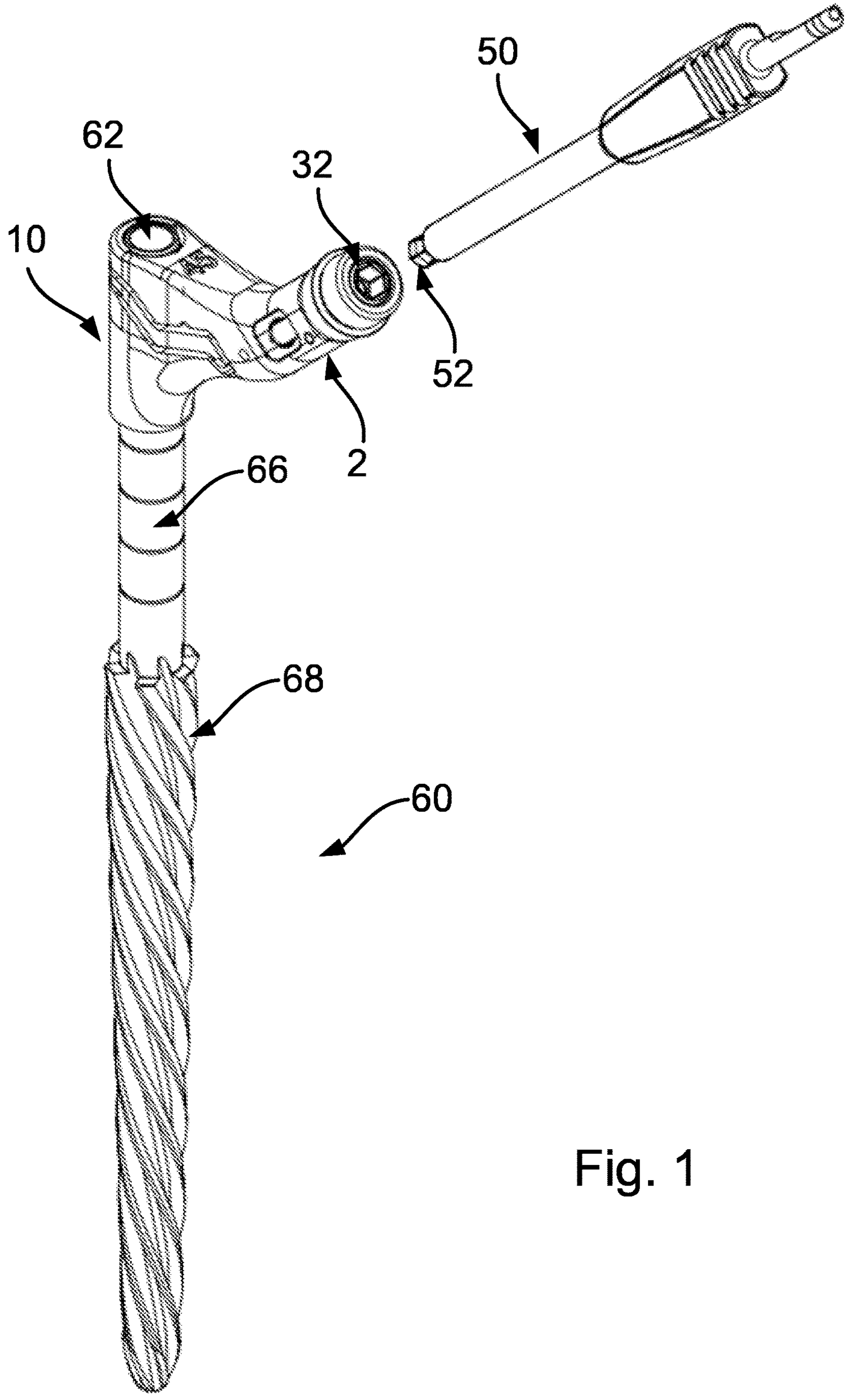
FIG. 1 shows a trial neck attached to a femoral canal implement, such as a reamer, according to an embodiment of this disclosure.
Figure 2:
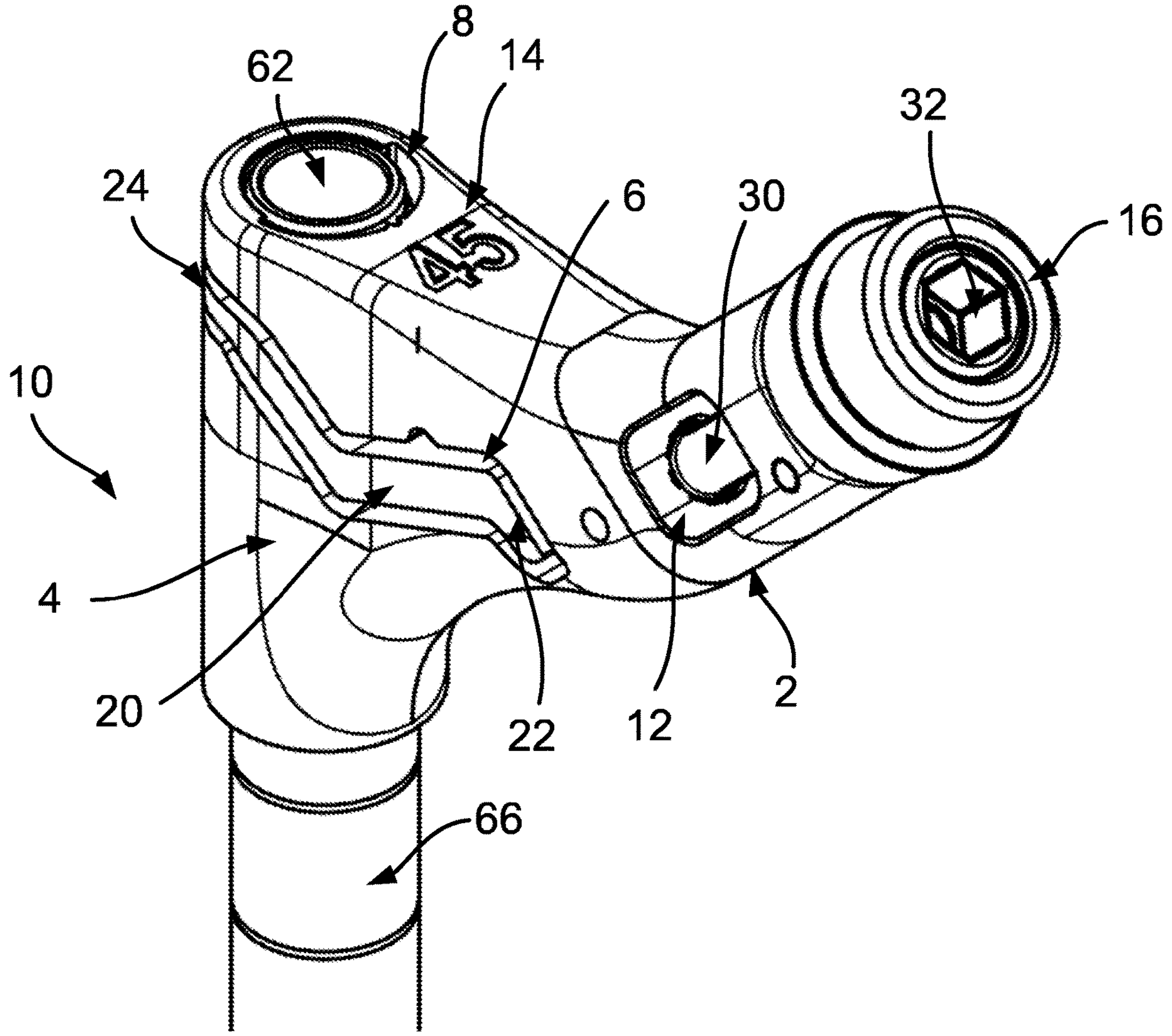
FIG. 2 shows another view of the trial neck of FIG. 1.
Figure 3:
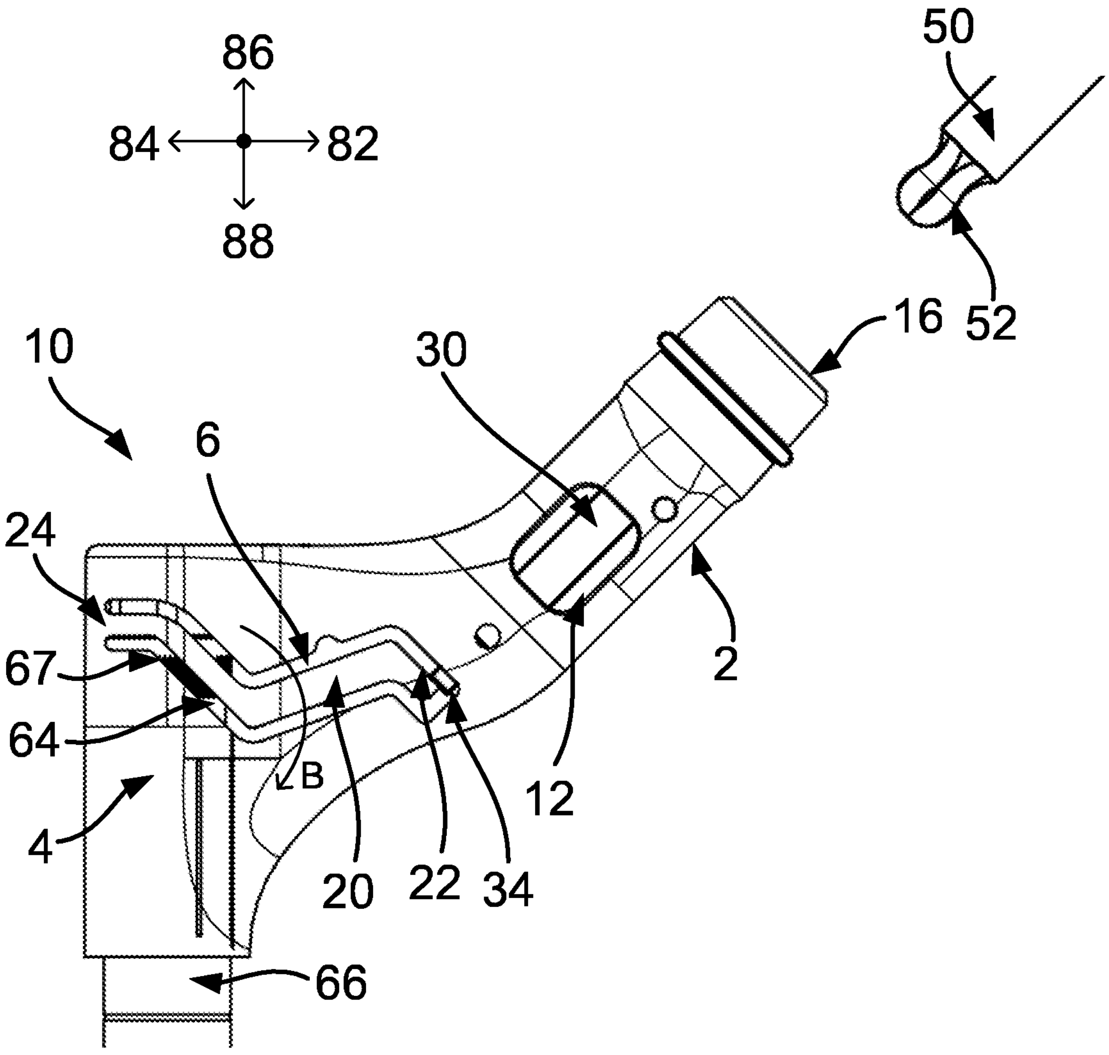
FIG. 3 shows an anterior view of the trial neck of FIG. 1.
Figure 4A:
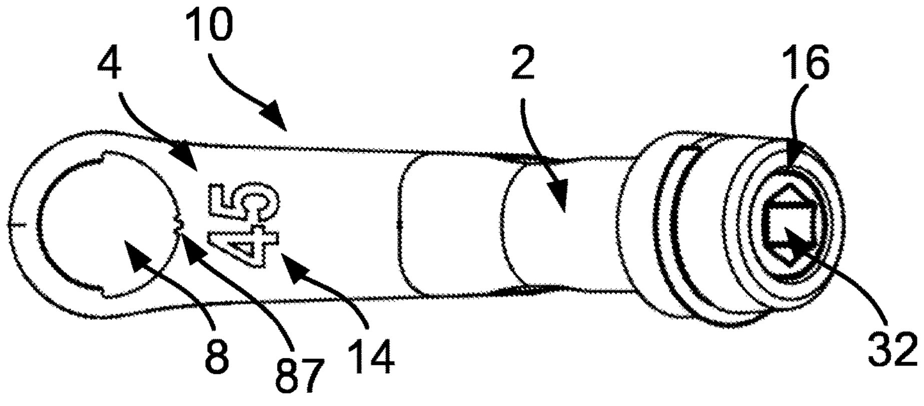
FIG. 4A shows a superior view of the trial neck of FIG. 1.
Figure 4B:
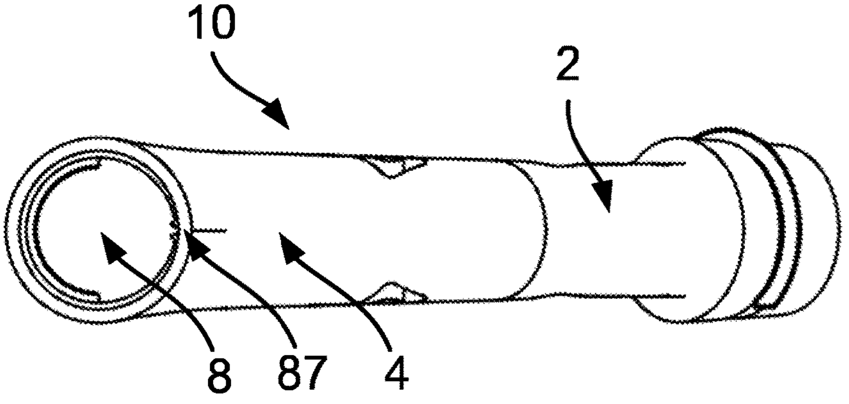
FIG. 4B shows an inferior view of the trial neck of FIG. 1.
Figure 4C:
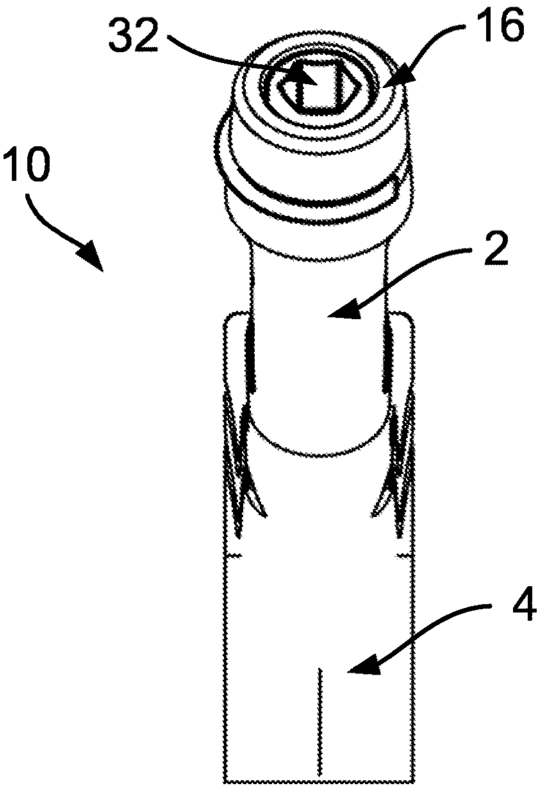
FIG. 4C shows a medial view of the trial neck of FIG. 1.

Embodiments of this disclosure are described in the following with reference to the accompanying drawings.

Various views of a trial neck 10 and a femoral canal implement according to an embodiment of this disclosure are shown in FIGS. 1 to 7. In the Figures, the following directions are indicated:

medial direction 82;

lateral direction 84;
superior direction 86; and
inferior direction 88

The femoral canal implement may, for example, be a femoral canal preparation instrument such as a reamer, a trial stem, or a broach. The femoral canal implement may alternatively, for example, be an implant such as a stem implant.

In the following description of FIGS. 1 to 7, the femoral canal implement is a femoral canal preparation instrument comprising a reamer 60. However, it will be appreciated that in other embodiments, the femoral canal implement may be another implement such as one of the implements noted above and may have a proximal end that is configured similarly to the proximal end 64 of the reamer 60.

Figure 5:
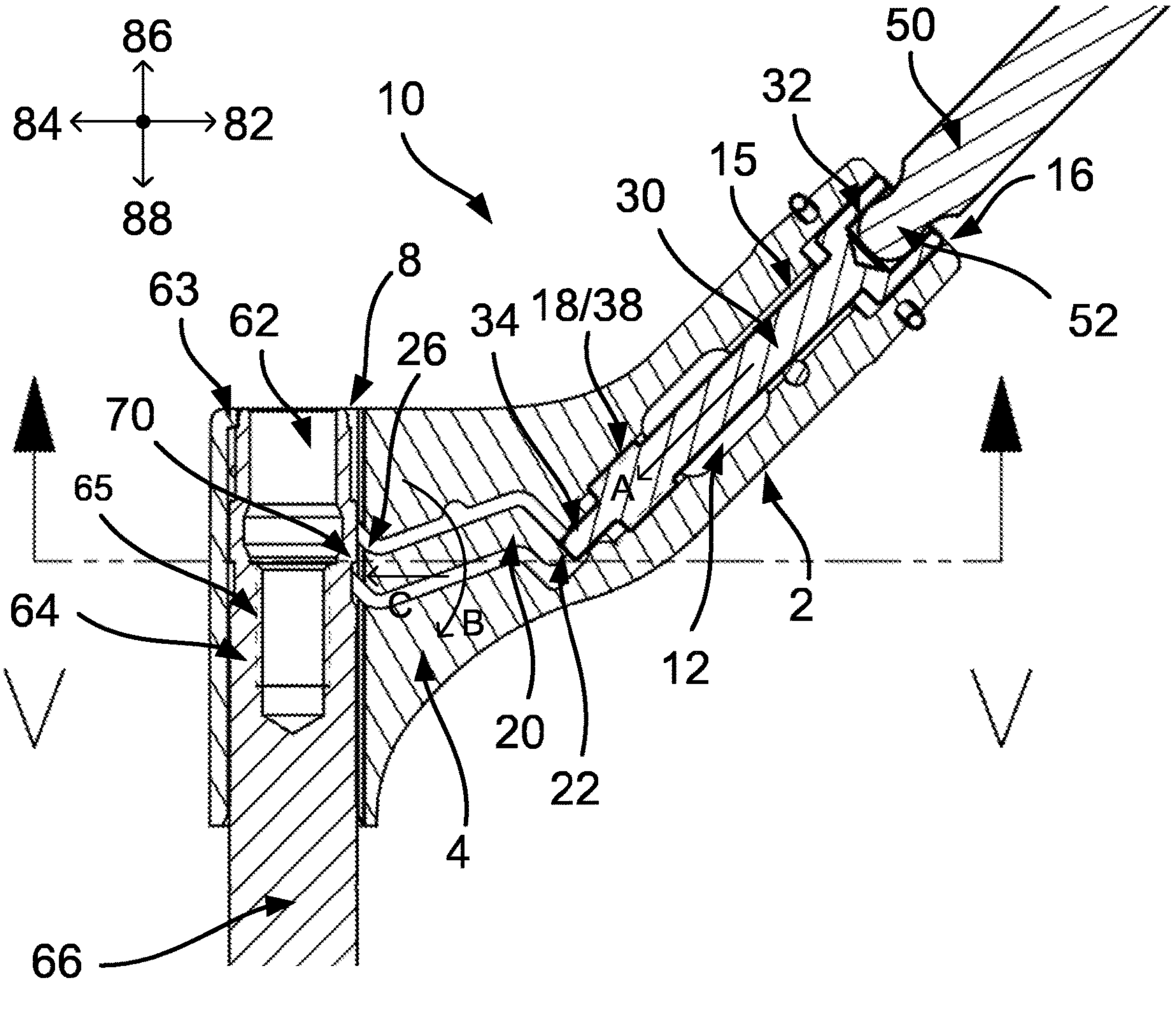
FIG. 5 shows a cross section of the trial neck of FIG. 1.

The trial neck 10 has a body portion 4. The body portion 4 includes a bore 8. The bore 8 may be a blind bore (closed at its proximal end), although in the embodiments shown in the Figures it is an open bore, which passes completely through the body portion 4. The bore 8 can receive the proximal end of a reamer 60, for attaching the reamer 60 to the trial neck 10. As shown in FIG. 5, in some embodiments, the bore may include an internal lip or shoulder 63 comprising a narrowed portion of the bore 8. The lip or shoulder 63 may engage with a corresponding lip or shoulder comprising an wider portion of the proximal end 64 of the femoral canal implement, to act as a dead stop preventing the proximal end 64 from passing completely through the bore 8.

The reamer 60 itself may be in the form of an elongate shaft (e.g. see FIG. 1) and may have a cutting surface 68 located distally. The reamer 60 may also have an intermediate part 66 located proximally with respect to the cutting surface 68. The reamer 60 has a proximal end 64. The proximal end 64 may be located proximally with respect to the cutting surface 68 and/or the intermediate part 66. The proximal end 64 may be substantially cylindrical, with a circular cross section, although this is not essential. The proximal end 64 may be inserted into the bore 8 of the trial neck 10 for attaching the reamer 60 to the trial neck, as will be described in more detail below.

As can be seen in FIG. 5, the proximal end 64 of the reamer 60 may include a number of features. For instance, the proximal end 64 may have a connection feature 62, such as a profiled bore, for attaching the reamer 60 to a reamer driver. The bore of the connection feature 62 may include an internal screw thread 65, to aid attachment of auxiliary instruments such as a reamer driver. In embodiments in which the bore 8 extends completely through the body portion 8, the reamer driver may be attached to the reamer 60 using the connection feature 62 even when the trial neck 10 is attached to the reamer 60.

The proximal end 64 of the reamer 60 also may include a circumferential lip or groove 70 for engagement with an engagement surface of the locking mechanism of the trial neck 10 to be described in detail below. As can be seen in FIG. 5, the lip or groove 70 may be formed by an edge of a circumferential part of the proximal end 64 of the reamer 60 that has a stepped increase (or decrease) in the radius of the proximal end 64.

In some embodiments, the reamer 60 may include a surface which is angled to conform with the engagement surface of the locking mechanism, at the angle at which the engagement surface contacts the reamer 60. The angled surface may comprise a circumferential (e.g. annular) indentation which extends around the reamer 60 (in much the same way as the lip or groove 70). In this way, the contacting surface areas of the reamer 60 and the engagement surface can be maximised, and potential damage to the surface of the reamer 60 (caused by the engagement surface "digging in to" the reamer 60) can be avoided. In some embodiments, the engagement surface and angled surface may cooperate to urge the internal lip or shoulder 63 against the corresponding lip or shoulder of the proximal end 64, thereby locking the proximal end 64 against movement in either axial direction within the bore 8.

The trial neck 10 also has an elongate neck 2. The elongate neck 2 extends from the body portion 4. The elongate neck 2 extends at a non-zero angle relative to a longitudinal axis of the bore 8. A proximal end 16 of the elongate neck 2 may be configured (i.e. include connection feature(s)) to be attached to a trial head.

The trial neck 10 may include one or more external indicia 14 for indicating information about the type, or dimensions of the trial neck 10. In the embodiment shown in FIGS. 1 to 7, one such indicium 14 is located on a proximal (superior) surface of the trial neck 10, although other locations for such indicia are possible.

As noted previously, the proximal end 64 of the reamer 60 may be received within the bore 8 for attaching the reamer 60 to the trial neck 10. According to embodiments of this disclosure, the trial neck 10 includes a locking mechanism. The locking mechanism can be used to lock the proximal end 64 of the reamer 60 within the bore 8, so as to prevent movement of the reamer 60 with respect to the trial neck 10 and/or inadvertent decoupling of the trial neck 10 from the reamer 60.

The locking mechanism comprises a lever 20. The lever 20 has a first end 24, a second end 22 and an engagement surface 26. The first end 24 may be located laterally with respect to the engagement surface 26 and the second end 22. The engagement surface 26 may be located laterally with respect to the second end 22.

In this embodiment, the first end 24 is integral with the body portion 4. As may be appreciated from a review of FIGS. 2, 3, 6 and 7, the first end 24 of the lever 20 may comprise a pair of arms which each extend around the bore 8 to join with the body portion 4 at a point located generally laterally on the trial neck 10. The point(s) at which the (pair of arms of) the first end 24 join the body portion 4 may form the hinge of a live spring.

The second end 22 in this embodiment is located within the elongate neck 2 of the trial neck 10, although it may be located in the body portion 4. Locating the second end 22 within the elongate neck 2 can allow the second end 22 sufficiently far away from the engagement surface 26 to allow the mechanical advantage provided by the lever 20 to be improved, compared to the location of the second end 22 of the lever 20 within the body portion 4.

In this embodiment, the engagement surface 26 is located intermediate the first end 24 and the second end 22. The engagement surface 26 in this embodiment is located adjacent a side wall of the bore 8, allowing the engagement surface 26 to come in to contact with and urge against the proximal end 64 of the reamer 60 to secure the proximal end 64 of the reamer 60 within the bore 8 when the lever 20 is actuated.

In the present embodiment, the aforementioned pair of arms of the lever 20, which extend round the bore 8, extend generally in the lateral direction 84 from the part of the lever 20 including the engagement surface 26, so as to join with the body portion 4 at the first end 24. The part of the lever 20 between the engagement surface 26 and the second end 22 may comprise a single solid piece, which bifurcates at the engagement surface 26 to form the pair of arms. The lever may thus be substantially fork-shaped or Y-shaped when viewed along the along the longitudinal axis of the bore 8.

As can be seen from the Figures, the part of the lever 20 between the engagement surface 26 and the second end 22 may include a number of dog leg type bends. This can allow a mechanical advantage to be gained from the actuation of the second end 22 of the lever 20 as described below, while also allowing the lever 20 to navigate the aforementioned non-zero angle between the elongate neck 2 and the longitudinal axis of the bore 8.

As can also be seen from the Figures, the lever 20 may reside in a slot formed in the side walls of the trial neck 10. The slot may be dimensioned with enough clearance to ensure that the lever 20 can be actuated without fouling the sides of the slot during operation of the locking mechanism. The slot may also be dimensioned so as to provide appropriate support for the lever 20 during washing of the trial neck 10.

In some embodiments, the locking mechanism also includes an actuation member 30. The actuation member 30 can be used to actuate the second end of the lever 20.

In the present embodiment, the trial neck 10 has a further bore 15 within which the actuation member 30 extends. The further bore 15 may extend substantially parallel to a (longitudinal) neck axis of the elongate neck 2. The further bore 15 may terminate at the proximal end 16 of the elongate neck 2. An opening to the further bore 15 located in this embodiment at the proximal end 16 of the elongate neck 2 may allow access to the actuation member 30. A proximal end of the actuation member 30 may comprise a connection feature 32 for connecting a corresponding connection feature 52 of a tool 50 to the actuation member 30 for actuating the actuation member 30. In some embodiments, a trial head, which is attachable to the proximal end 16 of the elongate neck 2, may include an opening or aperture, which passes through the trial head so as to provide access to the connection feature 32 for operating the actuation member 30. For instance, the tool 50 may be inserted through the opening or aperture in the trial head, to couple the connection feature 52 to the connection feature 32. In some embodiments, the tool 50 may be incorporated into the trial head itself.

To operate the actuation member 30, it may be moved along the further bore 15 (in the direction shown by the arrow "A" in FIG. 5, which in this embodiment is substantially parallel to the longitudinal axis of the elongate neck 2) towards the second end 22 of the lever 20. A tip 34 may thus come into contact with the second end 22 of the lever 20 thereby to deflect the lever 20. This causes the lever 20 to rotate around the first end 24 of the lever 20 (in the direction shown by the arrow "B" in FIG. 5). This in turn causes the engagement surface 26 to urge against the proximal end 64 of the reamer 60 to lock the proximal end 64 within the bore 8.

The further bore 15 may have a threaded surface 18 for engaging with a corresponding threaded surface 38 of the actuation member 30. Rotation of the actuation member 30 within the further bore 15 (e.g. using the tool 50) can cause the actuation member to move back and forth within the further bore 15, and along the direction "A" as noted above, thereby to operate the lever 20.

In some embodiments, the trial neck may include one or more windows. For instance, the trial neck 10 in the embodiment shown in the drawings has a window 12 located in the elongate neck 2. The window 12 may open out onto both an anterior and a posterior surface of the elongate neck 10. The window 12 may allow the actuation member 30 to be viewed within the further bore 15. This can allow the position of the actuation member 30 within the further bore 15 to be determined by inspection. The window(s) 12 may also allow improved access to the interior of the trial neck 10 (particularly the further bore 15) for cleaning operations. Note that the aforementioned slot, within which the lever 20 may be located, may similarly allow access to the interior of the trial neck 10 for improved cleaning operations.

Figure 6:
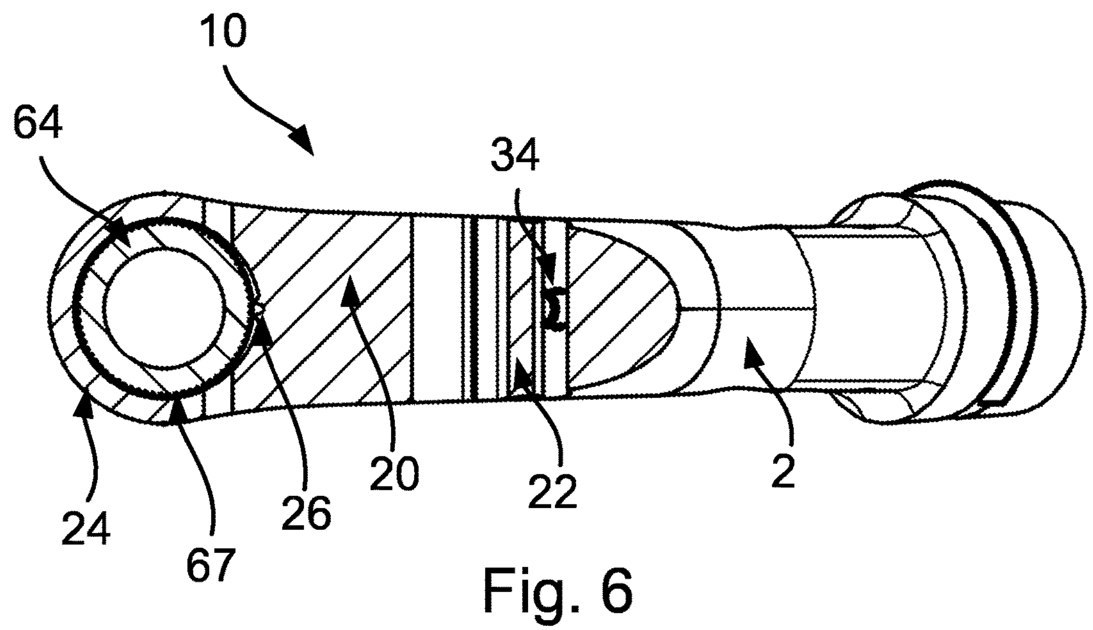
FIG. 6 shows another cross section of the trial neck of FIG. 1, through the plane V-V indicated in FIG. 5.
Figure 7:
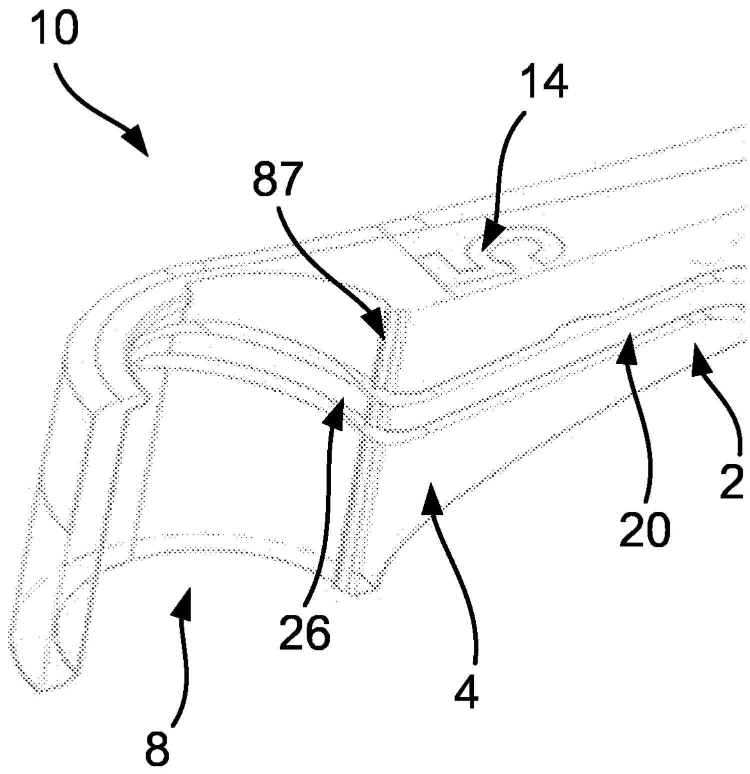
FIG. 7 is a cross section of the trial neck of FIG. 1, showing a profiled surface of the bore of the trial neck, for engaging with a corresponding profile surface of the femoral canal implement.

In some embodiments, the engagement surface 26 of the lever 20 may be curved (an example of this in the present embodiment can be seen in FIGS. 6 and 7. This can allow the engagement surface substantially to conform with a curved outer surface of the proximal end 64 of the reamer 60. By conforming with the curved outer surface of the proximal end 64 of the reamer 60, the size of the area of engagement between the engagement surface 26 and the proximal end 64 may be increased, for a more secure connection between the trial neck 10 and the reamer 60. Note that a part of the engagement surface 26 located on the aforementioned pair of arms of the lever 20 may form at least part of the curved engagement surface 26 in some embodiments.

The locking mechanism described above generally opposes movement of the reamer 60 along the longitudinal axis of the bore 8, thereby to prevent inadvertent movement of the trial neck 10 relative to the reamer 60 and/or to prevent inadvertent removal of the proximal end of the reamer 60 from the bore 8. In some embodiments, the trial neck 10 and/or the reamer 60 may include features for opposing rotation of the reamer 60 withing the bore 8 (i.e. around the longitudinal axis of the bore 8). Note that even in the absence of such additional features, the frictional force associated with the urging of the engagement surface 26 against the proximal end of the reamer 60 may to some extent also oppose rotation of the reamer 60 within the bore 8.

In the embodiment shown in FIGS. 1 to 7 (see, in particular, FIGS. 4A, 4B and 7), an inner surface of the bore 8 has a profiled surface 87 for engaging with a corresponding profiled outer surface 67 (see FIGS. 3 and 6) of the proximal end 64 of the reamer 60. Engagement of these profiled surfaces 67/87 can resist rotation of the reamer 60 with respect to the trial neck 10 about a longitudinal axis of the bore 8/reamer 60 as noted above. The profiled surface 67 on the reamer 60 may extend completely around the circumference of the proximal end 64 of the reamer 60 (as can be seen in FIG. 6) so that part of the profiled surface 67 may be presented to the profiled surface 87 of the trial neck 10, irrespective of the orientation of the proximal end 64 of the reamer 60 when it is first inserted into the bore 8.

As may be seen in FIG. 7, the profiled surface 87 need not extend around the circumference of the bore 8, but instead may be present only on a segment of the bore 8 (in FIG. 7, the segment including the profiled surface 87 is a most medially located part of the inner surface of the bore 8). As may also be seen in FIG. 7, the profiled surface 87 may extend completely along a length of the inner surface of the bore 15. In the embodiment shown in FIGS. 1 to 7, the profiled surface 87 extends from a proximal end of the bore 8 to a distal end of the bore 8, and part of the profiled surface 87 is located on the engagement surface 26. However, it is also envisaged that the profiled surface 87 may only be located on the engagement surface 26.

As described above, the proximal end 64 of the reamer 60 may include a circumferential lip or groove 70 for engagement with an engagement surface of the locking mechanism of the trial neck 10. As can be seen in FIG. 5, the lip or groove 70 may be formed by an edge of a circumferential part of the proximal end 64 of the reamer 60 that has a stepped increase (or decrease) in the radius of the proximal end 64. In some embodiments, the profiled surface 67 may be located on this lip and/or in this groove 70, for engagement with the (part of) the profiled surface 87 on the engagement surface 26 of the lever 20. Note that in some embodiments, the engagement surface may catch against the lip or groove 70 (e.g. the part of the lever 20 including the engagement surface 26 may slot into the groove 70) when the locking mechanism is locked, to resist removal of the proximal end 64 of the reamer 60 from the bore 8. In this way, in addition to the frictional force applied by the engagement surface 26, the engagement surface 26 may physically block the removal of the proximal end 64 of the reamer 60 from the bore 8.

The profiled surfaces 67/87 may comprise correspondingly shaped splines, which run substantially parallel to the longitudinal axes of the reamer 60 and the bore 8. Other kinds of profiled surfaces may be used. Note that the (part of) the profiled surface 87 on the engagement surface 26 may form a tooth or teeth, which engage with the profiled surface 67 on the proximal end 64 of the reamer 60 (e.g. see FIG. 6).

Figure 8:
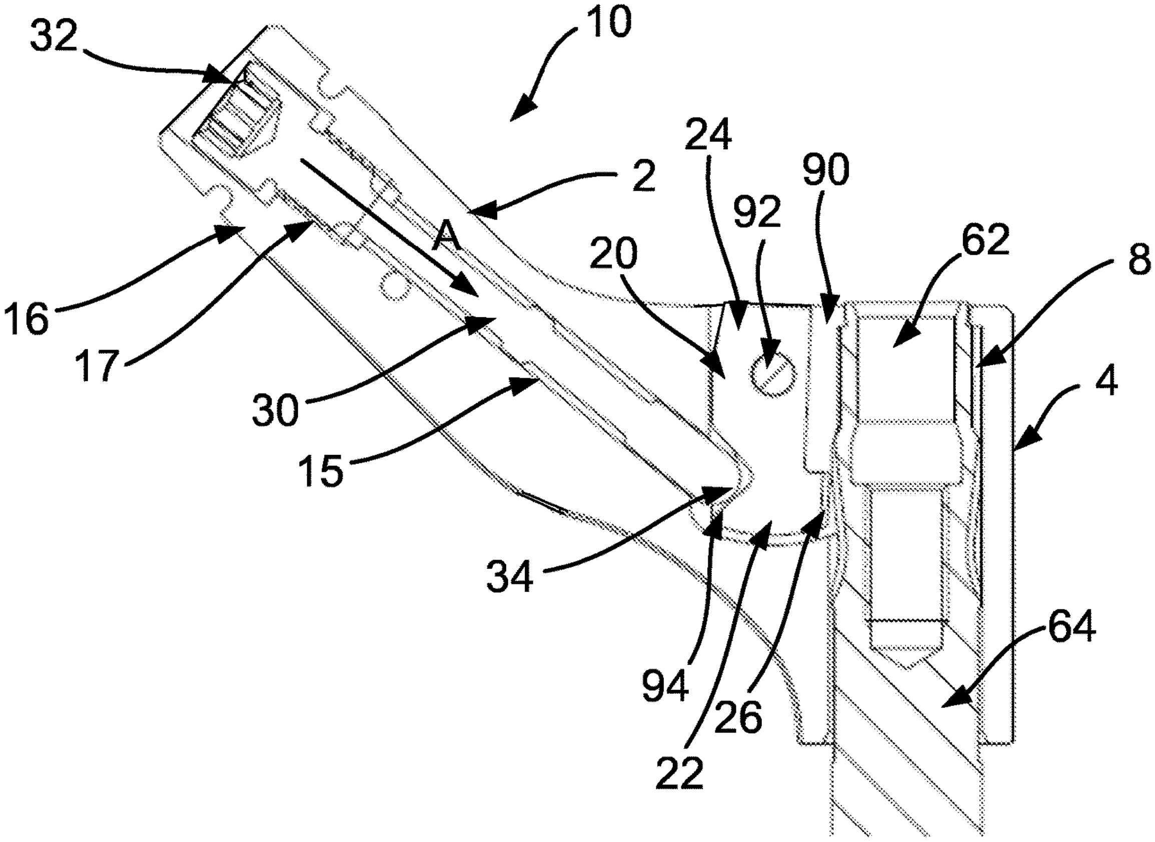
FIG. 8 shows a cross section of a trial neck according to another embodiment of this disclosure.
Figure 9:
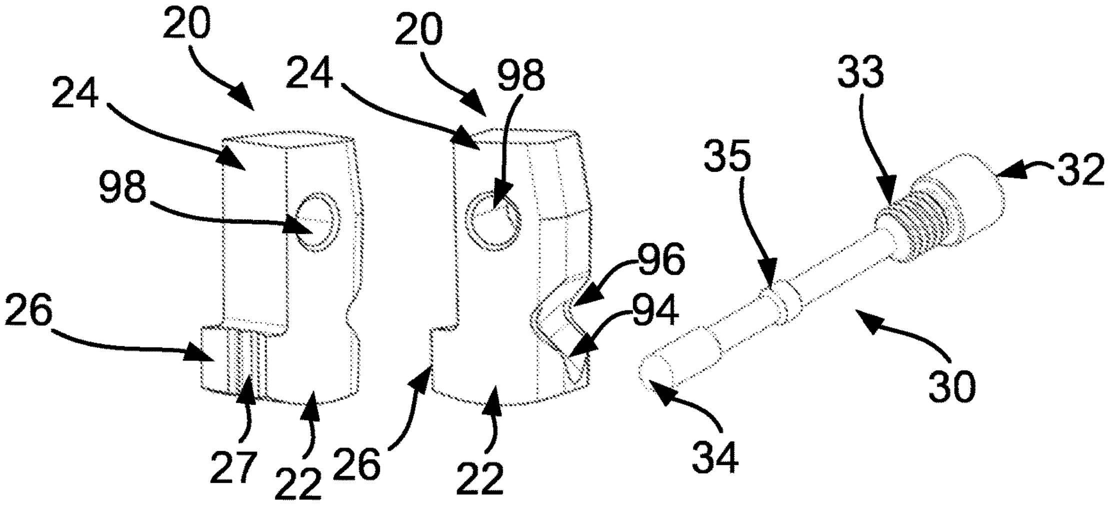
FIG. 9 shows some of the components of the trial neck of FIG. 8 in more detail.
Figure 10:
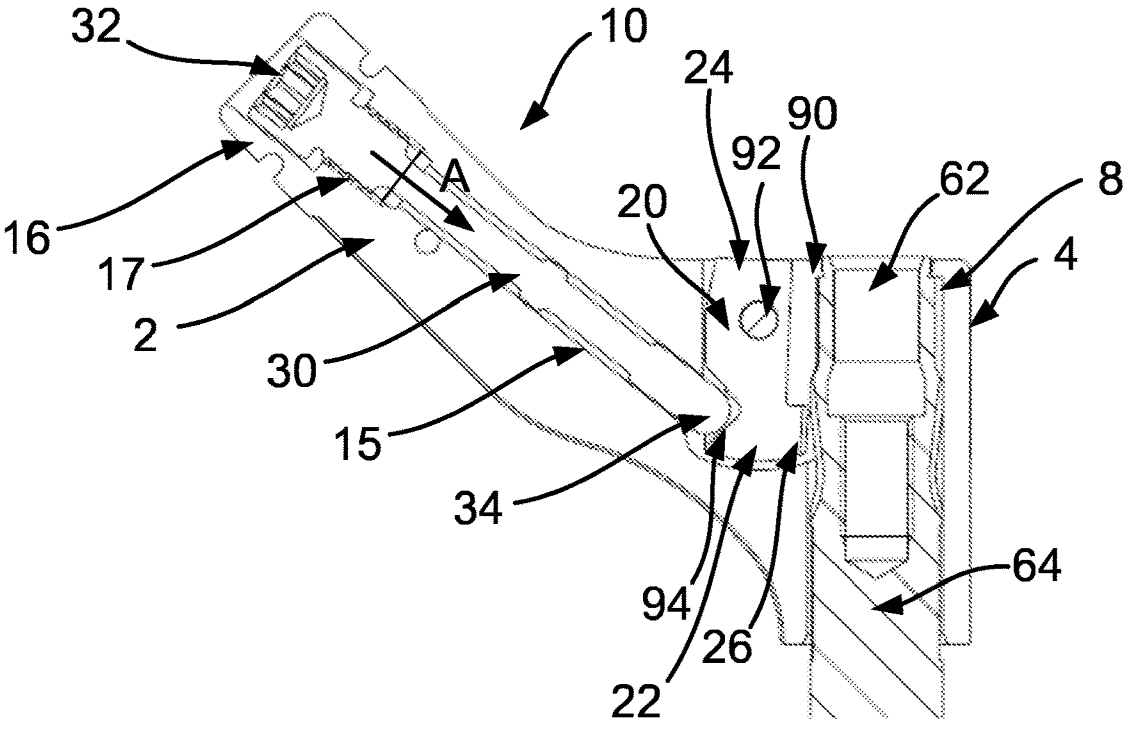
FIG. 10 shows a cross section of the trial neck of FIG. 8 in an unlocked configuration.

FIG. 8 shows a cross section of a trial neck according to another embodiment of this disclosure. FIG. 9 shows some of the components of the trial neck of FIG. 8 in more detail. FIG. 10 shows a cross section of the trial neck of FIG. 8 in an unlocked configuration, while FIG. 11 shows a cross section of the trial neck of FIG. 8 in a locked configuration.

Figure 11:
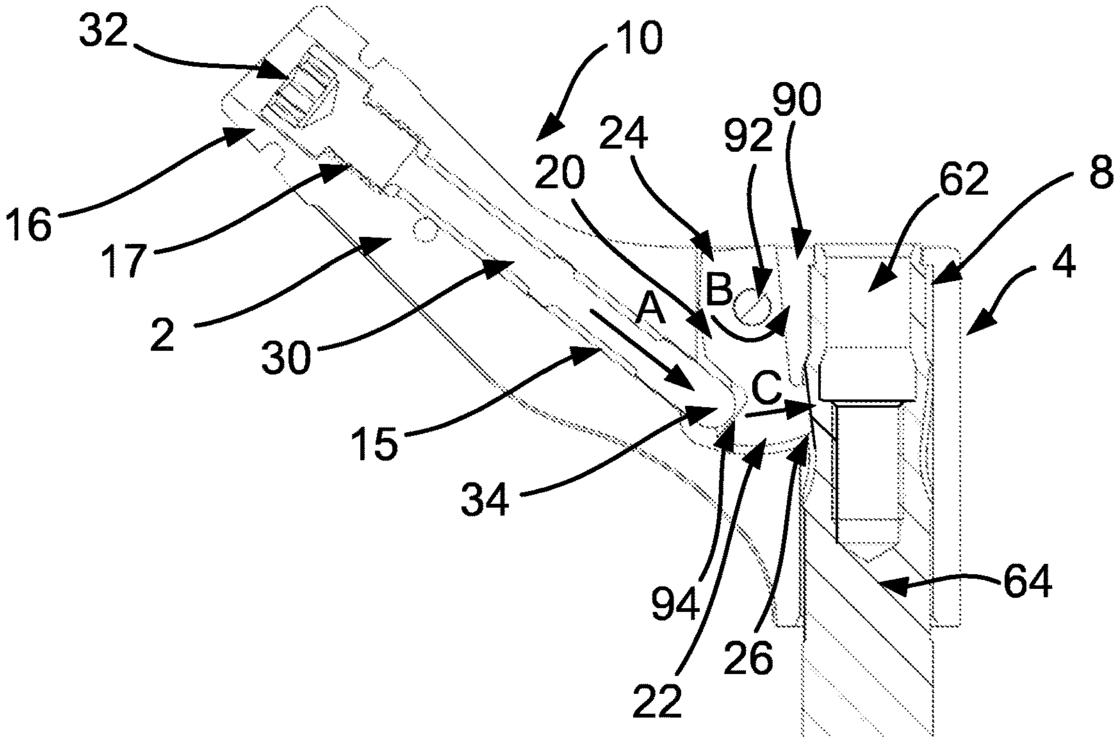
FIG. 11 shows a cross section of the trial neck of FIG. 8 in a locked configuration.

The femoral canal implement shown in FIGS. 8, 10 and 11 may, for example, be a femoral canal preparation instrument comprising reamer, a trial stem, or a broach. The femoral canal implement shown in FIGS. 8, 10 and 11 may alternatively, for example, be an implant such as a stem implant.

In the following description of FIGS. 8 to 11, the femoral canal implement comprises a reamer, such as the reamer 60 shown in FIG. 1. However, it will be appreciated that in other embodiments, the femoral canal implement may be one of the other implements noted above and may have a proximal end that is configured similarly to the proximal end 64 of the reamer.

The trial neck 10 has a body portion 4. The body portion 4 includes a bore 8. The bore 8 may be a blind bore (closed at its proximal end), although in the embodiment shown in FIGS. 8, 10 and 11 it is an open bore, which passes completely through the body portion 4. The bore 8 can receive the proximal end 64 of the reamer, for attaching the reamer to the trial neck 10. As described above, the bore 8 may include an internal lip or shoulder comprising a narrowed portion of the bore 8. The lip or shoulder may engage with a corresponding lip or shoulder comprising an wider portion of the proximal end 64 of the femoral canal implement, to act as a dead stop preventing the proximal end 64 from passing completely through the bore 8.

The reamer itself may be in the form of an elongate shaft (e.g. see FIG. 1) and may have a cutting surface 68 located distally. The femoral canal implement 60 may also have an intermediate part 66 located proximally with respect to the cutting surface 68. The femoral canal implement 60 has a proximal end 64. The proximal end 64 may be located proximally with respect to the cutting surface 68 and/or the intermediate part 66. The proximal end 64 may be substantially cylindrical, with a circular cross section, although this is not essential. The proximal end 64 may be inserted into the bore 8 of the trial neck 10 for attaching the femoral canal implement 60 to the trial neck, as will be described in more detail below.

As can be seen in FIGS. 8, 10 and 11, the proximal end 64 of the reamer may include a number of features. For instance, the proximal end 64 may have a connection feature 62, such as a profiled bore, for attaching the reamer to a reamer driver. The bore of the connection feature 62 may include an internal screw thread, to aid attachment of the reamer driver. In embodiments in which the bore 8 extends completely through the body portion 4, the reamer driver may be attached to the reamer using the connection feature 62 even when the trial neck 10 is attached to the reamer.

The proximal end 64 of the reamer also may include a circumferential lip or groove for engagement with an engagement surface of the locking mechanism of the trial neck 10, as described above in relation to FIGS. 1 to 7.

As described above, the reamer may include a surface which is angled to conform with the engagement surface of the locking mechanism, at the angle at which the engagement surface contacts the reamer. The angled surface may comprise a circumferential (e.g. annular) indentation which extends around the reamer (in much the same way as the lip or groove 70). In this way, the contacting surface areas of the reamer and the engagement surface can be maximised, and potential damage to the surface of the reamer (caused by the engagement surface "digging in to" the reamer) can be avoided.

The trial neck 10 also has an elongate neck 2. The elongate neck 2 extends from the body portion 4. The elongate neck 2 extends at a non-zero angle relative to a longitudinal axis of the bore 8. A proximal end 16 of the elongate neck 2 may be configured (i.e. include connection feature(s)) to be attached to a trial head.

As described in relation to FIGS. 1 to 7, the trial neck 10 may include one or more external indicia for indicating information about the type, or dimensions of the trial neck 10.

As noted previously, the proximal end 64 of the reamer may be received within the bore 8 for attaching the reamer to the trial neck 10. According to embodiments of this disclosure, the trial neck 10 includes a locking mechanism. The locking mechanism can be used to lock the proximal end 64 of the reamer within the bore 8, so as to prevent movement of the reamer with respect to the trial neck 10 and/or inadvertent decoupling of the trial neck 10 from the reamer.

The locking mechanism comprises a lever 20. The lever 20 has a first end 24, a second end 22 and an engagement surface 26. The first end 24 may be located superiorly with respect to the engagement surface 26 and the second end 22. The engagement surface 26 may be located on a laterally facing side of the lever 20.

The lever 20 may be pivotably mounted (e.g. at the first end 24 of the lever 20) within the trial neck 10, for instance within the body portion 4. In the embodiments shown in FIGS. 8 to 16, the lever 20 is pivotably mounted within a cavity 90 located in a part of the body portion 4 that adjoins the elongate neck 2 and that is adjacent the bore 8. At least part of the cavity 90 may open out into the bore 8, so as to allow engagement surface 26 to engage with the proximal end 64 of a femoral canal implement 60 when the latter is received within the bore 8. As before, this can allow the engagement surface 26 to come in to contact with and urge against the proximal end 64 of the femoral canal implement 60 to secure the proximal end 64 of the femoral canal implement 60 within the bore 8 when the lever 20 is actuated.

The pivot mounting 92 may, for instance comprise a screw or bolt passing through the trial neck 10 in an anterior-posterior direction. The pivot mounting 92 may pass through a bore in the lever 20, to allow the lever to pivot substantially within the coronal plane.

In some embodiments, the locking mechanism also includes an actuation member 30. The actuation member 30 can be used to actuate the second end 22 of the lever 20, as will be described in more detail below. The actuation member 30 may be similar to the actuation member 30 describe above in relation to the embodiment of FIGS. 1 to 7. Thus, the trial neck 10 may have a further bore 15 within which the actuation member 30 extends. The further bore 15 may extend substantially parallel to a (longitudinal) neck axis of the elongate neck 2. The further bore 15 may terminate at the proximal end 16 of the elongate neck 2. An opening to the further bore 15 located in this embodiment at the proximal end 16 of the elongate neck 2 may allow access to the actuation member 30. A proximal end of the actuation member 30 may comprise a connection feature 32 for connecting a corresponding connection feature 52 of a tool 50 to the actuation member 30 for actuating the actuation member 30. In some embodiments, a trial head, which is attachable to the proximal end 16 of the elongate neck 2, may include an opening or aperture, which passes through the trial head so as to provide access to the connection feature 32 for operating the actuation member 30. For instance, the tool 50 may be inserted through the opening or aperture in the trial head, to couple the connection feature 52 to the connection feature 32. In some embodiments, the tool 50 may be incorporated into the trial head itself. As with the embodiment of FIGS. 1 to 7, the actuation member 30 may include a threaded surface 17 which engages with a corresponding inner threaded surface of the further bore 15, such that rotation of the actuation 30 within the further bore 15 (e.g. using the tool 50) causes the actuation member 30 to move along the further bore 5, thereby to operate the lever 20.

To operate the actuation member 30, it may be moved along the further bore 15 (in the direction shown by the arrow "A" in FIG. 8, which in this embodiment is substantially parallel to the longitudinal axis of the elongate neck 2) towards the second end 22 of the lever 20. A tip 34 of the actuation member 30 may thus come into contact with the second end 22 of the lever 20 thereby to move the lever 20. This causes the lever 20 to rotate around the pivot mounting 92 (in the direction shown by the arrow "B" in FIG. 11). This in turn causes the engagement surface 26 to urge (as indicated by the arrow labelled "C" in FIG. 11) against the proximal end 64 of the femoral canal implement 60, to lock the proximal end 64 within the bore 8. To release the proximal end 64 of the femoral canal implement 60, the actuation member 30 may be withdrawn along the further bore 15 (i.e. in the opposite direction to the direction indicated by the arrow labelled "A" in FIGS. 8, 10 and 11), allowing the lever 20 to pivot back in the opposite direction to the direction indicated by the arrow labelled "B" in FIG. 11, thereby to disengage the engagement surface 26 from the proximal end 64.

As noted above, in some embodiments, the engagement surface 26 of the lever 20 may be curved. This can allow the engagement surface substantially to conform with a curved outer surface of the proximal end 64 of the femoral canal implement 60. By conforming with the curved outer surface of the proximal end 64 of the femoral canal implement 60, the size of the area of engagement between the engagement surface 26 and the proximal end 64 may be increased, for a more secure connection between the trial neck 10 and the femoral canal implement 60.

As with the embodiment of FIGS. 1 to 7, the locking mechanism described above generally opposes movement of the femoral canal implement 60 along the longitudinal axis of the bore 8, thereby to prevent inadvertent movement of the trial neck 10 relative to the femoral canal implement 60 and/or to prevent inadvertent removal of the proximal end of the femoral canal implement 60 from the bore 8. As also noted above, in some embodiments, the trial neck 10 and/or the femoral canal implement 60 may include features for opposing rotation of the femoral canal implement 60 within the bore 8 (i.e. around the longitudinal axis of the bore 8). Note that even in the absence of such additional features, the frictional force associated with the urging of the engagement surface 26 against the proximal end of the femoral canal implement 60 may to some extent also oppose rotation of the femoral canal implement 60 within the bore 8.

In the embodiments shown in FIGS. 8 to 16 an inner surface of the bore 8 may have a profiled surface of the kind described above (e.g. profiled surface 87) for engaging with a corresponding profiled outer surface (e.g. profiled outer surface 67) of the proximal end 64 of the femoral canal implement 60. As described above, engagement of these profiled surfaces can resist rotation of the femoral canal implement 60 with respect to the trial neck 10 about a longitudinal axis of the bore 8/femoral canal implement 60. As also noted above, it is envisaged that the profiled surface (e.g. profiled surface 87) may only be located on the engagement surface 26.

Again, the profiled surfaces may comprise correspondingly shaped splines, which run substantially parallel to the longitudinal axes of the femoral canal implement 60 and the bore 8. Other kinds of profiled surfaces may be used. Note that the (part of) the profiled surface 87 on the engagement surface 26 may form a tooth or teeth (e.g. see the teeth 27 in FIG. 9), which engage with the profiled surface on the proximal end 64 of the femoral canal implement 60.

As described above in relation to the embodiment of FIGS. 1 to 7, the proximal end 64 of the femoral canal implement 60 may include a circumferential lip or groove for engagement with an engagement surface of the locking mechanism of the trial neck 10.

In the present embodiment, the actuation member may be provided with a widened portion 35 located intermediate proximal end of the actuation member 30 and the tip 34. This widened portion 35 may have a diameter which is substantially the same as the diameter of the further bore 15. This can assist in ensuring that a longitudinal axis of the actuation member 30 remains substantially parallel to a longitudinal axis of the further 15 bore 15 while the actuation member 30 moves within the further bore 15. At least some of the other parts of the actuation member 30 may have a narrower profile than the profile of the further bore, so as to reduce friction between the actuation member 30 and the further bore 15.

In the present embodiment, the lever 20 may include features for assisting the engagement of the second end 22 of the lever 20 with the tip 34 of the actuation member 30. With reference to FIG. 9 and to the cross sections shown in FIGS. 8, 10 and 11, the second end 22 of the lever 20 in this embodiment includes an actuation member receiving opening 96. The actuation member receiving opening 96 is located on a medial side of the lever 20, and is positioned such that the tip 32 of the actuation member 30 may slide into the actuation member receiving opening 96 as the actuation member 30 is moved in the direction indicated by the arrow labelled "A" in FIGS. 8, 10 and 11. The actuation member receiving opening 96 may have a funnel-shaped profile, to guide the tip 32 toward inner surface 94. The tip 32 may engage with, and urge against, the inner surface 94 to actuate the lever 20. Inner surface 94 itself may be angled such that a surface normal of the inner surface 94 is substantially parallel to a longitudinal axis of the actuation member 30 when, for instance, the engagement surface 26 is engaged with the proximal end 64 of the femoral canal implement 60. The funnel-shaped profile of the actuation member receiving opening 96 and the aforementioned orientation of the inner surface 94 may assist in ensuring that there is little or no movement of the actuation member 30 and/or the lever 20 outside the coronal plane while the actuation member 30 and the lever 20 are being operated.

In some embodiments, features may be included to assist in the correct rotation of the lever 20. For instance, features may be provided to prevent the lever 20 from interfering with the insertion or removal of the proximal end 64 of the femoral canal implement 60 into/out of the bore 8. Certain examples of such features will now be described in relation to FIGS. 12 to 16.

Figure 12:
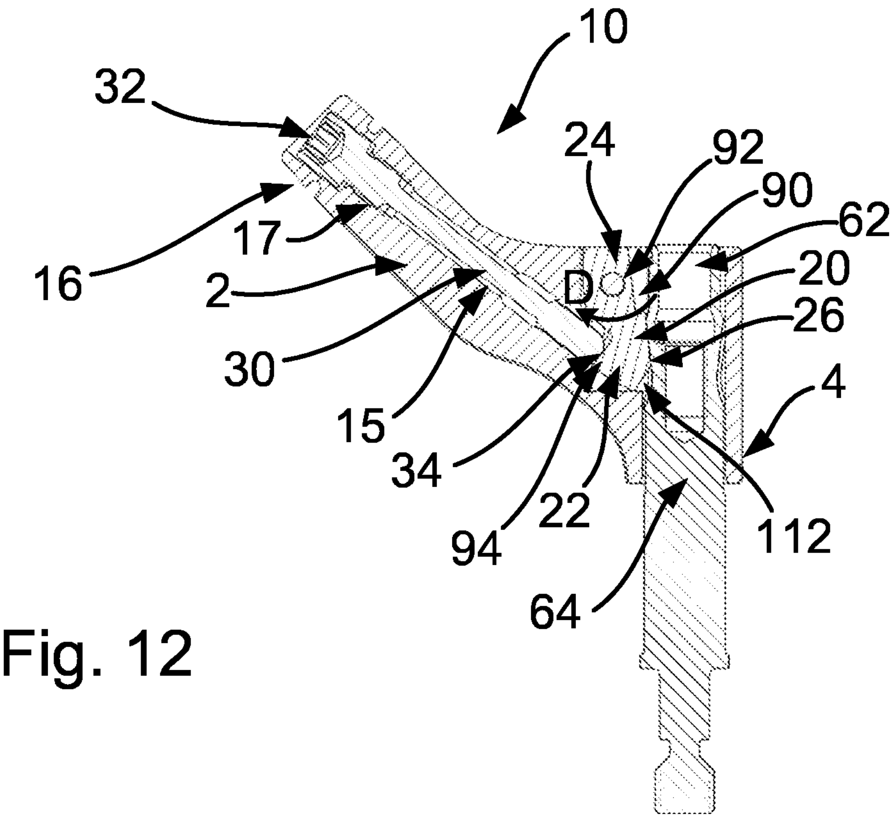
FIG. 12 shows a cross section of a trial neck according to a further embodiment of this disclosure.

FIG. 12 shows a cross section of a trial neck 10 according to a further embodiment of this disclosure. The embodiment of FIG. 12 is similar in many respects to the embodiment of FIGS. 8 to 11 and only the substantive differences will be described here.

In this embodiment, the second end 22 of the lever 20 includes an angled surface 112. The angled surface 112 faces toward the bore 8. In use, as the proximal end 64 of the femoral canal implement 60 is inserted into the bore 8, the proximal end 64 urges against and rides upon the angled surface 112, thereby to cause the lever 20 to pivot in the direction shown in FIG. 12 by the arrow labelled "D". This has the effect of moving the engagement surface 26 away from the proximal end 64 of the femoral canal implement 60. This can prevent the lever 20, and in particular the engagement surface 26 from spoiling against the proximal end 64 of the femoral canal implement 60 as is it is inserted into the bore 8.

Although the angled surface 112 has been described in relation to FIG. 12, it will be appreciated that an angled surface of this kind may be included in any of the embodiments shown in FIGS. 8 to 16.

Figure 13:
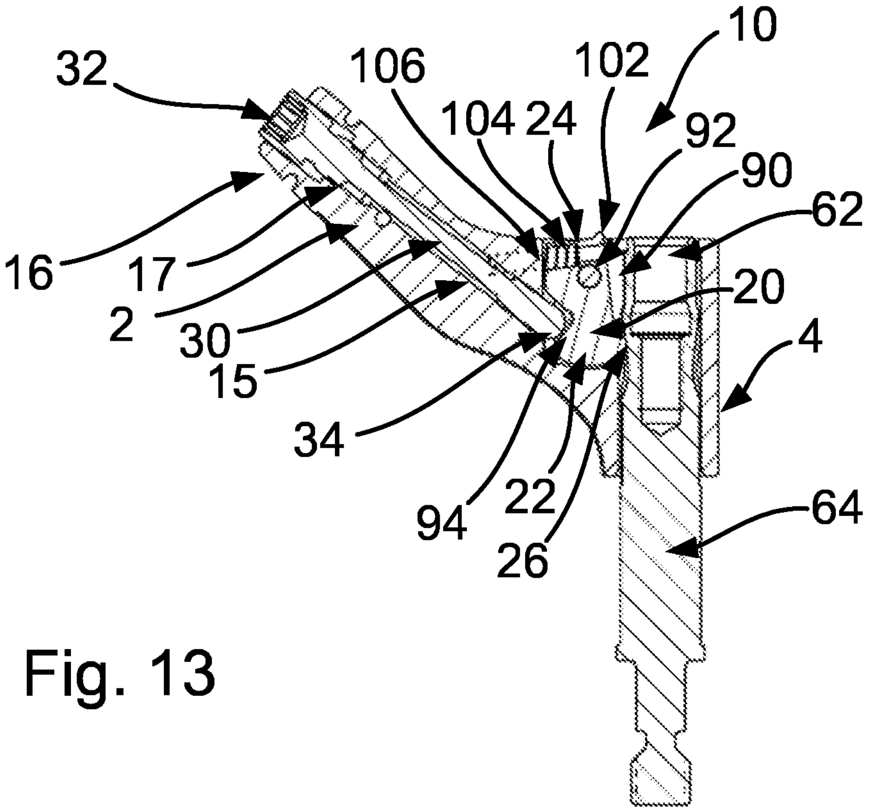
FIG. 13 shows a cross section of a trial neck according to another embodiment of this disclosure.

FIG. 13 shows a cross section of a trial neck 10 according to another embodiment of this disclosure. The embodiment of FIG. 13 is similar in many respects to the embodiment of FIGS. 8 to 12 and only the substantive differences will be described here.

In this embodiment, the lever 20 further comprises a biasing element 104. The biasing element 104 in this embodiment is mounted on the medial side of the first end 24 of the lever 20. A first end of the biasing element 104 may urge against a medially located side 106 wall of the cavity 90, thereby the bias the lever 20 such that the first end 24 of the lever 20 is biased toward the bore 8, whereas the engagement surface 26 is biased away from the bore 8. In some embodiments, the first end of the biasing element 104 may be received in a blind bore located in the medially located side wall of the cavity 90. Similarly, a second end of the biasing element 104 may be received in a blind bore located in the first end 24 of the lever 20.

The biasing element 104 can operate to keep the engagement surface 26 away from the bore 8 prior to actuation of the actuation member 30. This can, for example, prevent the engagement surface 26 from spoiling against the proximal end 64 of the femoral canal implement 60 as is it is inserted into the bore 8.

Although the biasing element 104 has been described in relation to FIG. 13, it will be appreciated that a biasing element of this kind may be included in any of the embodiments shown in FIGS. 8 to 16.

The biasing element in FIG. 13 comprises a helical spring. However, it will be appreciated that other kinds of biasing element may be used.

Figure 14:
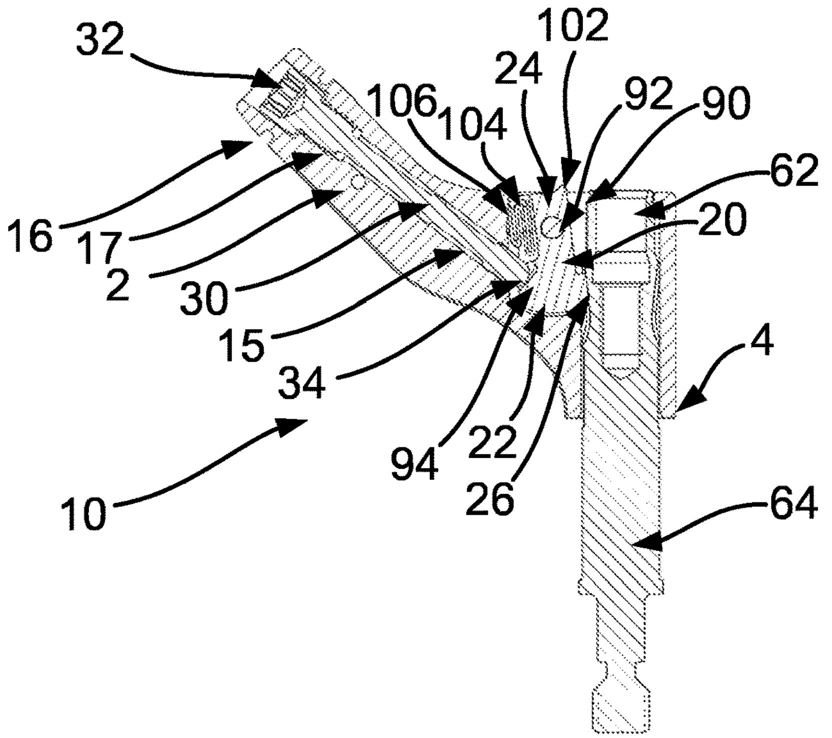
FIG. 14 shows a cross section of a trial neck according to a further embodiment of this disclosure.

FIG. 14 shows a cross section of a trial neck 10 according to a further embodiment of this disclosure. The embodiment of FIG. 14 is similar in many respects to the embodiment of FIGS. 8 to 13 and only the substantive differences will be described here.

In this embodiment, instead of the helical spring described above in relation to FIG. 13, the biasing element 104 comprises a leaf spring. As can be seen in FIG. 14, the leaf spring may include a meander pattern. The biasing element 104 in this example may be integrally formed with the lever 20.

Although the (leaf spring) biasing element 104 has been described in relation to FIG. 14, it will be appreciated that a biasing element of this kind may be included in any of the embodiments shown in FIGS. 8 to 16.

Figure 15:
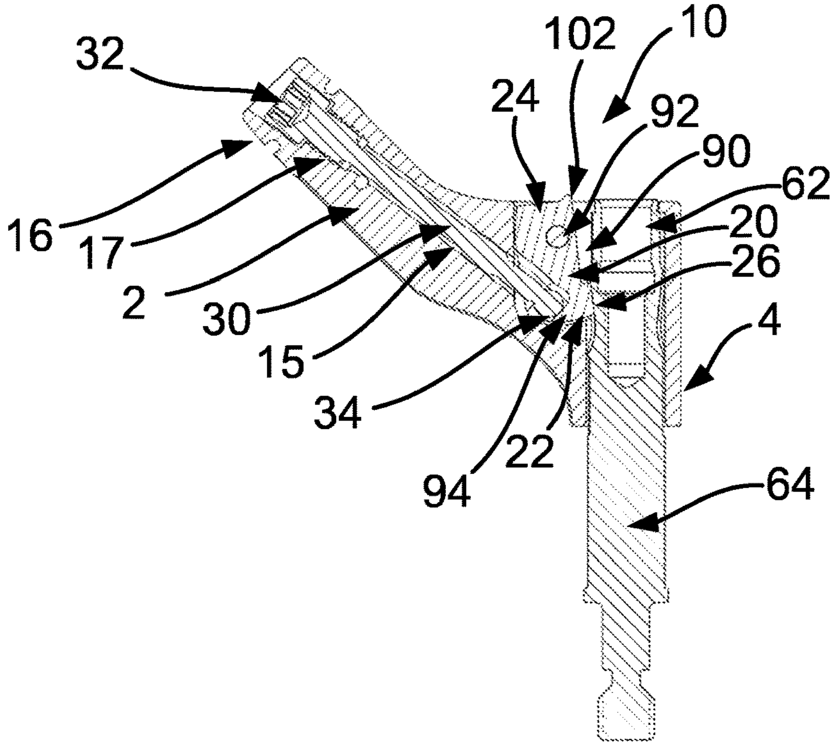
FIG. 15 shows a cross section of a trial neck according to another embodiment of this disclosure.

FIG. 15 shows a cross section of a trial neck 10 according to another embodiment of this disclosure. The embodiment of FIG. 15 is similar in many respects to the embodiment of FIGS. 8 to 14 and only the substantive differences will be described here.

In this embodiment, the first end 24 of the lever 20 includes a grippable feature 102. The grippable feature 102 in this embodiment comprises a protrusion, which extends superiorly from the body portion 4 to allow it to be operated manually by a surgeon. It is envisaged that other forms of grippable feature could be used, such as a profiled or roughened surface or a series of ridges.

The grippable feature 102 is manually operable by a surgeon to manually actuate the lever 20 so as to move the engagement surface 26 away from the proximal end 64 of the femoral canal implement 60. In particular, the surgeon may use the grippable feature 102 to rotate the first end 24 of the lever toward the bore 8, so that the engagement surface 26 pivots away from the bore 8.

In use, this can allow the surgeon to make sure that the engagement surface 26 does not spoil against the proximal end 64 of the femoral canal implement 60 as is it is inserted into the bore 8. The surgeon can also use the grippable feature 102 to make such that the engagement surface 26 is disengaged from the proximal end 64 of the femoral canal implement 60 before attempting to remove the proximal end 64 from the bore 8.

Although the grippable feature 102 has been described in relation to FIG. 15, it will be appreciated that a grippable feature of this kind may be included in any of the embodiments shown in FIGS. 8 to 16. Indeed, the embodiments shown in FIGS. 13, 14 and 16 each include such a feature.

Figure 16:
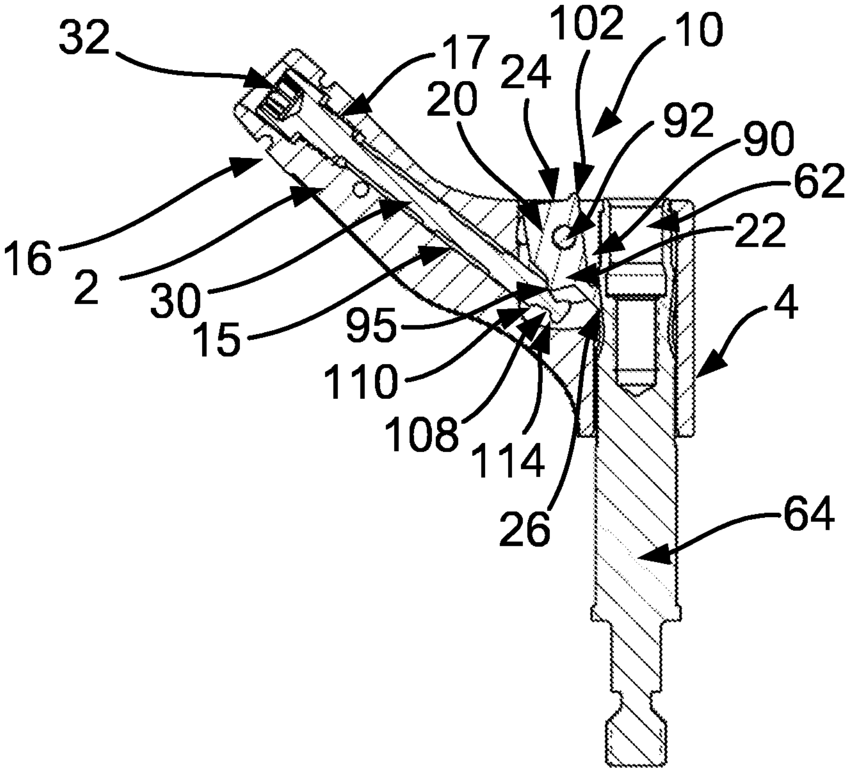
FIG. 16 shows a cross section of a trial neck according to a further embodiment of this disclosure.

FIG. 16 shows a cross section of a trial neck 10 according to a further embodiment of this disclosure. The embodiment of FIG. 16 is similar in many respects to the embodiment of FIGS. 8 to 14 and only the substantive differences will be described here.

In this embodiment, the actuation member 30 has a distal end (at which is located the tip 32) for engaging with the second end 22 of the lever 20 to actuate the lever 20. In this embodiment, the distal end also includes an indentation 108.

The indentation 108 in embodiment comprises a narrowed portion of the actuation member 30. The second end 22 of the lever 20 also includes a protrusion 95, which corresponds to the indentation 108.

In this embodiment, as the actuation member 30 moves toward the second end 22 of the lever 20, a proximal edge 110 of the indentation 108 contacts the protrusion 95, thereby to urge the engagement surface 26 against (see FIG. 16) the proximal end 64 of the femoral canal implement 60.

The indentation 108 can also operate to cause the lever 20 to pivot such that the engagement surface 26 is moved away from the proximal end 64 of the femoral canal implement 60 as the actuation member 30 is withdrawn along the further bore 15. In particular, as the actuation member 30 is withdrawn along the further bore 15, a distal edge 114 of the indentation 108 contacts the protrusion 95, thereby to cause the lever 20 to pivot such that the engagement surface 26 moves away from the proximal end 64 of the femoral canal implement 60.

The indentation 108 and the corresponding protrusion 95 may therefore cooperate to ensure that the engagement surface 26 disengages from the proximal end 64 of the femoral canal implement 60, so that the engagement surface 26 does not inhibit removal of the proximal end 64 of the bore 8.

Although the indentation and the corresponding protrusion have been described in relation to FIG. 16, it will be appreciated that an indentation and corresponding protrusion of this kind may be included in any of the embodiments shown in FIGS. 8 to 16. Indeed, the embodiment shown in FIG. 15 includes such a feature. In particular, in FIG. 15, the tip 32 of the actuation member 30 is substantially spherical. This forms a neck located immediately proximally from the tip 32, which constitutes an indentation of the kind described above. The corresponding protrusion in this embodiment may be formed by a lip of the actuation member receiving opening 96 described above. In this embodiment, as the actuation member 30 is withdrawn along the further bore 15, the indentation formed by the neck can act against the lip of the actuation member receiving opening 96, thereby to rotate the engagement surface 26 of the lever 20 away from the femoral canal implement 60. Again, this can prevent the engagement surface 26 from resting against the femoral canal implement 60, which might otherwise inhibit correct removal of the proximal end 64 of the femoral canal implement 60 from the bore 8.

According to an embodiment of this disclosure, there may be provided a method of attaching a trial neck (e.g. a trial neck 10 of the kind described above in relation to FIGS. 1 to 16) to a femoral canal implement (such as the reamer 60 or any of the other femoral canal implements noted above). The method may include inserting the proximal end 64 of the femoral canal implement (e.g. reamer 60) into the bore 8 of the trial neck 10. The method may also include actuating the second end 22 of the lever 20 to urge the engagement surface 26 against the proximal end 64 of the femoral canal implement (e.g. reamer 60).

As noted above, the method may include actuating the second end 22 of the lever 20 using an actuation member, e.g. the actuation member 30. The method may also include connecting a tool (e.g. the tool 50) to the connection feature 32 of the actuation member 30 for actuating the actuation member 30. While using the trial neck 10, the method may also include viewing the actuation member 30 through a window (e.g. the window 12) in the elongate neck 2 of the trial neck 10. The method may further include cleaning the trial neck 10 before it is used (again). The window 12 may assist in this cleaning, by allowing improved access to the further bore 15 within which the actuation member 30 may be located.

According to an embodiment of this disclosure, there may be provided a surgical kit. The surgical kit may include a trial neck 10 of the kind described above in relation to FIGS. 1 to 16. The surgical kit may also include a femoral canal implement (e.g. a reamer 60) of the kind described above. It is envisaged that the kit may include further components (e.g. one or more differently sized trial necks of the kind described above, one or more different kinds of femoral canal implement (e.g. different reamers), one or more trial heads, and/or any other components).

Accordingly, there has been described a trial neck for hip surgery and a method of attaching a trial neck to a femoral canal implement. The trial neck includes a body portion including a bore for receiving a proximal end of a femoral canal implement. The trial neck also includes an elongate neck extending from the body portion. The trial neck further includes a locking mechanism comprising a lever. The lever has a first end, which may be integral with the body portion or which may be pivotably mounted. The lever also has a second end. The lever further has an engagement surface, which may be located intermediate the first end and the second end, or which may be located at the second end. The second end of the lever is actuable to urge the engagement surface against the proximal end of the femoral canal implement to secure the proximal end of the femoral canal implement within the bore.

Although particular embodiments of this disclosure have been described, it will be appreciated that many modifications/additions and/or substitutions may be made within the scope of the claims.

The invention claimed is:

1. A trial neck for hip surgery, the trial neck comprising:

a body portion including a bore for receiving a proximal end of a femoral canal implement;

an elongate neck extending from the body portion;

a locking mechanism comprising a lever having: (i) a first end; (ii) a second end; (iii)—an engagement surface; and (iv) an actuation member for engaging with the second end of the lever to actuate the lever;

a further bore extending within the elongate neck, wherein the actuation member extends within the further bore, wherein the second end of the lever is actuable to urge the engagement surface against the proximal end of the femoral canal implement to secure the proximal end of the femoral canal implement within the bore.

2. The trial neck of claim 1, wherein the further bore extends substantially parallel to a longitudinal axis of the elongate neck.

3. The trial neck of claim 1, wherein a proximal end of the elongate neck has an opening leading to the further bore, and wherein a proximal end of the actuation member comprises a connection feature for connecting a tool to the actuation member for actuating the actuation member.

4. The trial neck of claim 3, wherein the proximal end of the elongate neck is configured to be attached to a trial head.

5. The trial neck of claim 1, wherein:

the further bore has a threaded surface, and wherein the actuation member comprises a threaded surface for engaging with the threaded surface of the further bore to allow the actuation member to be rotated to move the actuation member along the further bore to engage with the second end of the lever.

6. The trial neck of claim 1, comprising a window for viewing the actuation member within the further bore.

7. The trial neck of claim 1, wherein the first end of the lever is located at a lateral side of the trial neck.

8. The trial neck of claim 1, wherein the engagement surface of the lever is curved to conform with a curved outer surface of the proximal end of the femoral canal implement.

9. The trial neck of claim 1, wherein an inner surface of the bore has a profiled surface for engaging with a corresponding profiled outer surface of the proximal end of the femoral canal implement to prevent rotation of the femoral canal implement with respect to the trial neck about a longitudinal axis of the femoral canal implement.

10. A trial neck for hip surgery, the trial neck comprising:

a body portion including a bore for receiving a proximal end of a femoral canal implement;

an elongate neck extending from the body portion;

a locking mechanism comprising a lever having: (i) a first end; (ii) a second end; and (iii) an engagement surface, wherein (i) the second end of the lever is actuable to urge the engagement surface against the proximal end of the femoral canal implement to secure the proximal end of the femoral canal implement within the bore, (ii) the first end of the lever is integral with the body portion, and (iii) the engagement surface is located intermediate the first end of the lever and the second end of the lever.

11. The trial neck of claim 10, wherein the second end of the lever is located within the elongate neck.

12. The trial neck of claim 10, wherein the lever includes at least one dog leg bend.

13. A trial neck for hip surgery, the trial neck comprising:

a body portion including a bore for receiving a proximal end of a femoral canal implement;

an elongate neck extending from the body portion;

a locking mechanism comprising a lever having: (i) a first end that is pivotably mounted within the trial neck; (ii) a second end; (iii) an engagement surface; and (iv) an actuation member, wherein (i) the second end of the lever is actuable to urge the engagement surface against the proximal end of the femoral canal implement to secure the proximal end of the femoral canal implement within the bore, (ii) the actuation member has a distal end for engaging with the second end of the lever to actuate the lever, and (iii) the distal end includes an indentation for engaging with a corresponding protrusion on the second end of the lever to move the engagement surface away from the proximal end of the femoral canal implement on withdrawal of the actuation member along the further bore.

14. The trial neck of claim 13, wherein the second end of the lever includes an actuation member receiving opening.

15. The trial neck of claim 13, wherein the first end of the lever includes a grippable feature for manually actuating the lever to move the engagement surface away from the proximal end of the femoral canal implement.

16. The trial neck of claim 13, wherein the second end of the lever includes an angled surface facing toward the bore, to allow the proximal end of the femoral canal implement to ride upon the angled surface to pivot the lever to move the engagement surface away from the proximal end of the femoral canal implement upon insertion of the proximal end of the femoral canal implement into the bore.

17. The trial neck of claim 13, wherein the lever further comprises a biasing element for biasing the first end of the lever toward the bore, thereby to bias the engagement surface away from the bore.

* * * * *